(12) United States Patent
Breuer et al.

(10) Patent No.: US 7,189,545 B2
(45) Date of Patent: Mar. 13, 2007

(54) PRODUCTION AND USE OF PYRUVATE DECARBOXYLASE

(75) Inventors: Michael Breuer, Limburgerhof (DE); Bernhard Hauer, Fussgönheim (DE); Thomas Friedrich, Darmstadt (DE)

(73) Assignee: BASF Aktiengesellschaft (DE)

( * ) Notice: Subject to any disclaimer, the term of this patent is extended or adjusted under 35 U.S.C. 154(b) by 256 days.

(21) Appl. No.: 10/488,007

(22) PCT Filed: Aug. 16, 2002

(86) PCT No.: PCT/EP02/09159

§ 371 (c)(1),
(2), (4) Date: Feb. 27, 2004

(87) PCT Pub. No.: WO03/020921

PCT Pub. Date: Mar. 13, 2003

(65) Prior Publication Data

US 2004/0219654 A1    Nov. 4, 2004

(30) Foreign Application Priority Data

Aug. 31, 2001    (DE) ................. 101 42 467

(51) Int. Cl.
*C12N 9/02* (2006.01)
*C12N 1/21* (2006.01)
*C12P 7/24* (2006.01)
*C07H 21/04* (2006.01)

(52) U.S. Cl. .................. 435/147; 435/132; 435/69.1; 435/189; 435/155; 536/23.2

(58) Field of Classification Search .............. None
See application file for complete search history.

(56) References Cited

U.S. PATENT DOCUMENTS 6,004,789 A    12/1999    Bruhn et al.

FOREIGN PATENT DOCUMENTS

| WO | WO 96/37620 | 11/1996 |
|---|---|---|
| WO | WO 99/09195 | 2/1999 |

OTHER PUBLICATIONS

Chang et al. (Biochem. 2000, 39, 9430-9437).*
Bruhn et al. "The replacement of Trp392 by alanine influences the decarboxylase/carboligase activity and stability of pyruvate decarboylase from Zymomonas mobilis" Sep. 12, 1995, pp. 650-655.
Iwan et al. "Studies on the continuous production of (R)-(-)-phenylacetylcarbinol in an enzyme-membrane reactor" Jan. 22, 2001, pp. 387-396.
Candy et al. "Structure and properties of pyruvate decarboxylase and site-directed mutagenesis of the Zymomonas mobilis enzyme" Feb. 25, 1998, pp. 323-338.

* cited by examiner

*Primary Examiner*—Rebecca E. Prouty
*Assistant Examiner*—Md. Meah
(74) *Attorney, Agent, or Firm*—Connolly Bove Lodge & Hutz, LLP

(57) ABSTRACT

A polypeptide with pyruvate decarboxylase activity, derived from the pyruvate decarboxylase from *Zymomonas mobilis* by substitution of an amino acid in position 553.

13 Claims, 1 Drawing Sheet

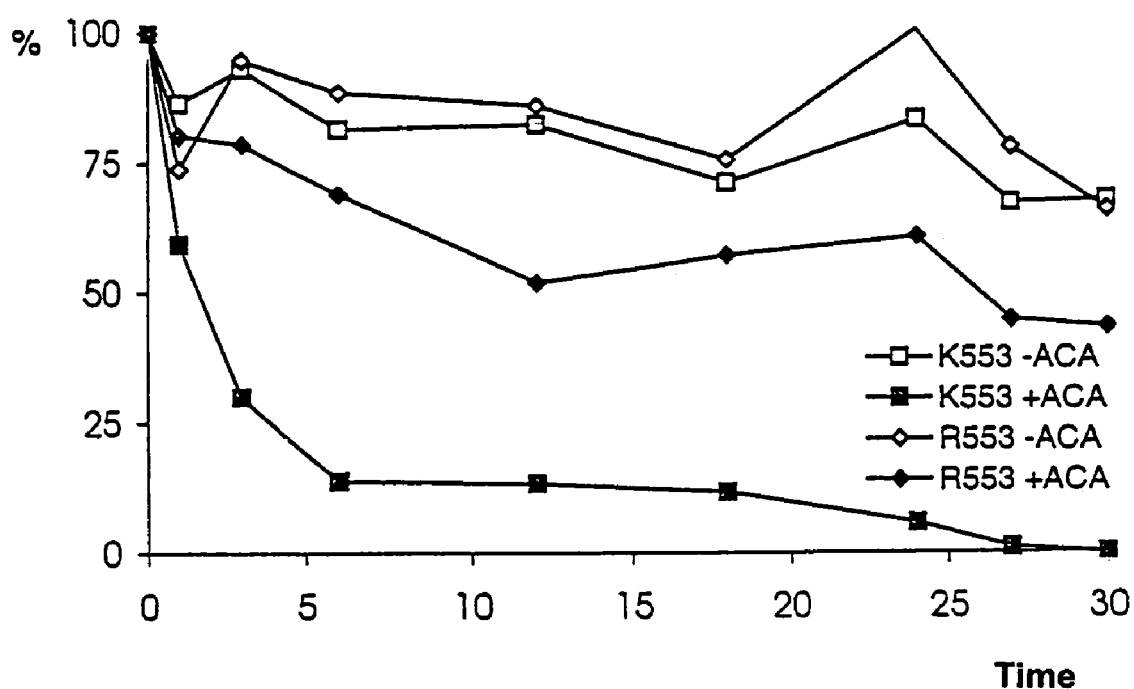

PRODUCTION AND USE OF PYRUVATE DECARBOXYLASE

FIELD OF THE INVENTION

The invention relates to a process for preparing acyloins by the enzymic conversion of alpha-ketocarboxylic acids and/or aldehydes in the presence of pyruvate decarboxylase (PDC), and to a novel PDC, which is suitable for this process, and its preparation.

DESCRIPTION OF THE BACKGROUND

Acyloins, or alpha-hydroxyketones, are compounds which possess an optically active C atom and which play a considerable role in the synthesis of more complex compounds, for example, and in particular, (R)-(−)-phenylacetylcarbinol (PAC), which is of great economic interest for producing ephedrine. The R enantiomer, which is formed by using *Saccharomyces cerevisiae* to fermentatively convert pyruvate in the presence of benzaldehyde (DE-PS 548 459 dated 1932), is required for this purpose.

In this synthesis of PAC using yeast cells, a large number of byproducts are formed as a result of the activity of the majority of the enzymes present in the yeast, and the growth of the cells is inhibited by the presence of benzaldehyde.

Even when it has been isolated from the yeast, the pyruvate decarboxylase (PDC) gives rise, in this reaction, to substantial proportions of 2-hydroxypropiophenone, which is an isomer of PAC.

Thiamine diphosphate-dependent and $Mg^{++}$-dependent PDC (E.C. 4.1.1.1) is widely distributed and is found in many plants, yeasts and other fungi and in some bacteria. It catalyzes the non-oxidative decarboxylation of pyruvate to acetaldehyde, and an acyloin condensation, with the formation of alpha-hydroxyketones, takes place as a side reaction.

An enzymic reaction of this nature also takes place when an aldehyde is used as the starting compound, instead of alpha-ketocarboxylic acids, and the aldehyde which is formed by the decarboxylation can also take part in the condensation reaction as a "cosubstrate", with the formation of homoacyloins R—CHOH—CO—R', in which R=R'.

WO 96/37620 describes the preparation of acyloins from acetaldehyde and benzaldehyde by catalysis using a recombinantly modified pyruvate decarboxylase obtained from *Zymomonas mobilis*. Those enzymes in which the tryptophan residue in position 392 has been replaced with a sterically smaller residue, such as alanine, glycine, phenylalanine, leucine, isoleucine, arginine, histidine, serine or threonine, are in particular described as being suitable. However, it is reported that acetaldehyde inactivates all these enzymes.

SUMMARY OF THE INVENTION

It was, therefore, an object of the present invention to provide novel pyruvate decarboxylases which do not exhibit the abovementioned disadvantages at all, or only exhibit them to a substantially lesser degree, without, however, the synthetic capacity of the novel enzymes being reduced.

We have found that this object is achieved by a pyruvate decarboxylase which, as compared with the *Zymomonas mobilis* PDC, carries an amino acid substitution at position 553, with the lysine at this position being replaced with an amino acid exhibiting similar space-filling and/or charge properties, in particular with the amino acid lysine or alanine.

Other embodiments and advantages of the invention are set forth in part in the description, which follows, and in part, may be obvious from this description, or may be learned from the practice of the invention.

DESCRIPTION OF THE DRAWING

FIG. 1. Depiction of loss of activity of protein R553.

DESCRIPTION OF THE INVENTION

These novel enzymes (PDC) can be prepared from the known *Zymomonas mobilis* PDC gene sequence using recombinant methods which are known to the skilled person, such as site-directed mutagenesis. In this regard, the experimental section in WO 96/37620, which describes the recombinant construction, expression and purification of a mutant PDC from *Zymomonas mobilis*, is hereby expressly incorporated by reference. The *Zymomonas mobilis* nucleic acid sequence encoding the PDC is shown, in the 5'-3' direction, on page 14 in WO 96/37620, with the first nucleotides Nos. 1 to 3 (ATG) constituting the start codon (methionine, amino acid position +1) for the translation and nucleotides 1705–1707 (TAG) forming the stop codon as shown in SEQ ID NO: 1. The amino acid sequence of the *Zymomonas mobilis* PDC can be obtained from this nucleotide sequence by translating it in accordance with the genetic code.

A preferred embodiment of the invention relates to a PDC in which the lysine (K) at position 553 has been replaced with arginine (R) (R553).

As compared with the starting molecule (K553), this enzyme exhibits superior stability toward acetaldehyde (FIG. 1), i.e. R553 loses substantially less activity in the presence of acetaldehyde (+ACA) than does K553.

A further advantage of this enzyme is that its synthetic performance (measurable as space/time yield) is substantially greater in a fed batch experiment than is that of K553.

Another object of the invention is a process for preparing enantiomerically pure phenylacetylcarbinols of the formula (I)

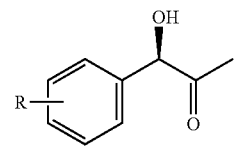

where R is H, F, Cl or Br, from acetaldehyde or pyruvate and benzaldehydes of the formula (II)

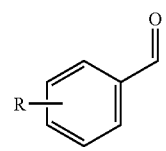

in the presence of the novel pyruvate decarboxylase.

Particularly suitable embodiments of this novel process are those in which acetaldehyde or pyruvate is subsequently metered in continuously or discontinuously, during the course of the biotransformation, such that the concentration of acetaldehyde or pyruvate in the reaction medium is between 20 and 50 mMol/l.

The following examples illustrate embodiments of the invention, but should not be viewed as limiting the scope of the invention.

As far as further details of this process are concerned, the reader is referred to WO 99/9195, which is hereby expressly incorporated by reference. The conduct of the novel process is essentially identical to that of the process described in WO 99/9195 apart from the catalyst employed (pyruvate decarboxylase).

EXAMPLE 1

Inactivating the PDC with Acetaldehyde

PDC 553R was treated with acetaldehyde under the following conditions:

30 mM acetaldehyde 50 mM morpholinoethanesulfonic acid 20 mM $MgCl_2$

20 µg cell-free crude protein extract dissolved in 100 µl of $H_2O$, pH 7.0

The incubation was carried out at 4° C. in order to prevent the enzyme-catalyzed acetoin formation reducing the concentration of acetaldehyde.

FIG. 1 depicts the loss of activity of the novel protein R553, as compared with the starting molecule K553, in the presence of acetaldehyde (+ACA). In the absence of acetaldehyde (−ACA), the two enzymes are equally stable over the observed period of 30 hours.

The invention claimed is:

1. A polypeptide, that possesses pyruvate decarboxylase activity, comprising a polypeptide encoded by the nucleic acid sequence of SEQ ID NO: 1 in which the lysine at position 553 is replaced with arginine.

2. A process for preparing enantiomerically pure phenylacetylcarbinols of formula (I):

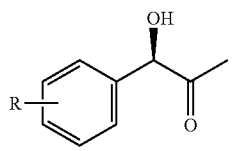

wherein R is H, F, Cl or Br, comprising combining in a reaction mixture an acetaldehyde or a pyruvate, and a benzaldehyde of formula (II):

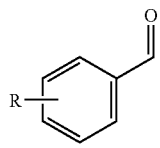

in the presence of the polypeptide of claim 1.

3. The process of claim 2, wherein the acetaldehyde or pyruvate is metered in continuously or discontinuously, during biotransformation, such that a concentration of acetaldehyde or pyruvate in the reaction medium is between 20 and 50 mMol/L.

4. The process of claim 2, wherein R is an H for said benzaldehyde.

5. The process of claim 2, which comprises combining the acetaldehyde with the benzaldehyde.

6. The process of claim 2, which comprises combining the pyruvate with the benzaldehyde.

7. The process of claim 5, wherein the acetaldehyde is metered in continuously during biotransformation, such that said concentration in the reaction medium is between 20 and 50 mMol/L.

8. The process of claim 6, wherein the pyruvate is metered in continuously during biotransformation, such that said concentration in the reaction medium is between 20 and 50 mMol/L.

9. The process of claim 5, wherein the acetaldehyde is metered in discontinuously during biotransformation, such that said concentration in the reaction medium is between 20 and 50 mMol/L.

10. The process of claim 6, wherein the pyruvate is metered in discontinuously during biotransformation, such that said concentration in the reaction medium is between 20 and 50 mMol/L.

11. A nucleic acid that encodes the polypeptide of claim 1.

12. A process for producing the polypeptide of claim 1 comprising isolating a polypeptide encoded by the nucleic acid sequence of SEQ ID NO: 1 from *Zymomonas mobilis* and replacing the amino acid at position 553 with arginine.

13. An isolated polypeptide, that possesses pyruvate decarboxylase activity, comprising a polypeptide encoded by the nucleic acid sequence of SEQ ID NO: 1 in which the lysine at position 553 is replaced with arginine.

\* \* \* \* \*

SEQUENCE LISTING

```
<160> NUMBER OF SEQ ID NOS: 1

<210> SEQ ID NO 1
<211> LENGTH: 1707
<212> TYPE: DNA
<213> ORGANISM: Zymomonas mobilis

<400> SEQUENCE: 1
atgagttata ctgtcggtac ctatttagcg gagcggcttg tccagattgg tctcaagcat      60
cacttcgcag tcgcgggcga ctacaacctc gtccttcttg acaacctgct tttgaacaaa     120
aacatggagc aggtttattg ctgtaacgaa ctgaactgcg gtttcagtgc agaaggttat     180
gctcgtgcca aaggcgcagc agcagccgtc gttacctaca gcgttggtgc gctttccgca     240
tttgatgcta tcggtggcgc ctatgcagaa aaccttccgg ttatcctgat ctccggtgct     300
ccgaacaaca acgaccacgc tgctggtcat gtgttgcatc acgctcttgg caaaaccgac     360
tatcactatc agttggaaat ggccaagaac atcacgccg ccgctgaagc gatttacacc     420
ccggaagaag ctccggctaa aatcgatcac gtgatcaaaa ctgctcttcg cgagaagaag     480
ccggtttatc tcgaaatcgc ttgcaacatt gcttccatgc cctgcgccgc tcctggaccg     540
gcaagtgcat tgttcaatga cgaagccagc gacgaagcat ccttgaatgc agcggttgac     600
gaaaccctga aattcatcgc caaccgcgac aaagttgccg tcctcgtcgg cagcaagctg     660
cgcgctgctg gtgctgaaga agctgctgtt aaattcaccg acgctttggg cggtgcagtg     720
gctactatgg ctgctgccaa gagcttcttc ccagaagaaa atgccaatta cattggtacc     780
tcatggggcg aagtcagcta tccgggcgtt gaaaagacga tgaaagaagc cgatgcggtt     840
atcgctctgg ctcctgtctt caacgactac tccaccactg gttggacgga tatccctgat     900
cctaagaaac tggttctcgc tgaaccgcgt tctgtcgttg tcaacggcat tcgcttcccc     960
agcgttcatc tgaaagacta tctgacccgt ttggctcaga aagtttccaa gaaaaccggt    1020
tctttggact tcttcaaatc cctcaatgca ggtgaactga agaaagccgc tccggctgat    1080
ccgagtgctc cgttggtcaa cgcagaaatc gcccgtcagg tcgaagctct tctgacccg     1140 aacacgacg ttattgctga aaccggtgac tcttggttca tgctcagcg catgaagctc      1200 ccgaacggtg ctcgcgttga atatgaaatg cagtggggtc acattggttg gtccgttcct    1260
gccgccttcg gttatgccgt cggtgctccg gaacgtcgca acatcctcat ggttggtgat    1320
ggttccttcc agctgacggc tcaggaagtt gctcagatgg ttcgcctgaa actgccggtt    1380
```

```
-continued atcatcttct tgatcaataa ctatggttac accatcgaag ttatgatcca tgatggtccg    1440
tacaacaaca tcaagaactg ggattatgcc ggtctgatgg aagtgttcaa cggtaacggt    1500
ggttatgaca gcggtgctgc taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                        1707
```